United States Patent [19]

Cooper et al.

[11] Patent Number: 5,342,953
[45] Date of Patent: Aug. 30, 1994

[54] N-2-CHLOROBENZYL-2-OXO AND N-2-CHLOROBENZYL-2,2-DIOXO-1,2,3-OXATHIAZOLIDINE DERIVATIVES, THEIR PREPARATION AND SYNTHESIS OF THIENO[3,2-C]PYRIDINE DERIVATIVES THEREFROM

[75] Inventors: Gary F. Cooper, Portola Valley; Keith E. McCarthy, Palo Alto, both of Calif.

[73] Assignee: Syntex (U.S.A.) Inc., Palo Alto, Calif.

[21] Appl. No.: 648,117

[22] Filed: Jan. 31, 1991

[51] Int. Cl.$^5$ .............................. C07D 241/04
[52] U.S. Cl. ............................ 548/122; 546/114
[58] Field of Search ............................ 548/122

[56] References Cited

U.S. PATENT DOCUMENTS 5,130,432  7/1992  Cooper et al. ................. 546/114

OTHER PUBLICATIONS

Potts, Comprehensive Heterocyclic Chemistry vol. 6 p. 933 (1984).

*Primary Examiner*—Robert Gerstl
*Attorney, Agent, or Firm*—David A. Lowin; Alan M. Krubiner

[57] ABSTRACT

Compounds of the formula:

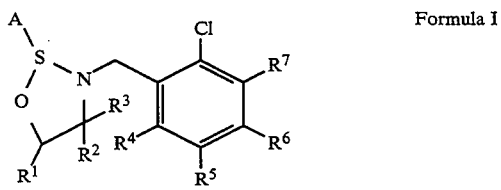

Formula I wherein:
A is oxo or dioxo;
$R^1$, $R^2$ and $R^3$ are independently hydrogen or lower alkyl of one to six carbon atoms;
$R^4$, $R^5$, $R^6$ and $R^7$ are independently hydrogen, lower alkyl of one to six carbon atoms, alkoxy, acyl or halo;

are advantageously converted to thieno[3,2-c]pyridine derivatives and the pharmaceutically acceptable salts thereof, particularly ticlopidine hydrochloride.

6 Claims, No Drawings

N-2-CHLOROBENZYL-2-OXO AND N-2-CHLOROBENZYL-2,2-DIOXO-1,2,3-OXATHIAZOLIDINE DERIVATIVES, THEIR PREPARATION AND SYNTHESIS OF THIENO[3,2-C]PYRIDINE DERIVATIVES THEREFROM

BACKGROUND OF THE INVENTION

1. Field of the Invention

The present invention relates to novel N-2-chlorobenzyl-2-oxo and N-2-chlorobenzyl-2,2-dioxo-1,2,3-oxathiazolidinyl derivatives and their use in the preparation of thieno[3,2-c]pyridine derivatives, particularly ticlopidine.

2. Background Information

Ticlopidine is a compound with desirable blood platelet aggregation inhibition qualities. Previous technology for the preparation of ticlopidine has entailed a low yielding, labor intensive process, employing certain potentially hazardous and expensive materials. The cost of preparing ticlopidine has, therefore, been high. It has been desired to provide improved synthetic process technology that allows for a higher conversion, reduced labor usage, and the elimination of costly, potentially dangerous materials.

A variety of synthetic approaches to making ticlopidine have been described in the art, including improvements on the various steps of such synthetic processes, e.g., as described below.

Ticlopidine was first described by Castaigne in U.S. Pat. No. 4,051,141, where the synthesis thereof was accomplished by condensation of a thieno[3,2-c]pyridine with o-chlorobenzyl chloride.

One desirable method of preparing ticlopidine calls for a N-substituted 2-(2'-thienyl)ethylamine as a key intermediate. The method involved conversion of 2-(2'-thienyl)ethanol to the corresponding sulfonate derivative and then to a secondary amine by reaction with o-chlorobenzylamine and cyclization to give ticlopidine free base, as described by Braye in U.S. Pat. No. 4,127,580.

Previous methods for the preparation of 2-(2'-thienyl)ethylamine have suffered from several disadvantages, including low yields (e.g., where the reactions resulted in mixtures of undesirable side products) and high cost.

For example, Braye, U.S. Pat. No. 4,128,561 describes a two-step process of making 2-(2'-thienyl)ethylamine by converting 2-(2'-thienyl)ethanol to N-2-(2'-thienyl)ethyl phthalimide, and then treating the phthalimide with diethylenetriamine to form the amine. Braye also describes the amination of 2-(2'-thienyl)alkyl sulfonates with ammonia at elevated temperature and pressure. Braye discloses problems encountered in the preparation of primary amines with ammonia, i.e., the tendency for the process to form secondary and tertiary amines as side products.

A process where 2-(2'-thienyl)ethylbromide is treated with alcoholic ammonia at ordinary temperature for 8 days to produce 2-(2'-thienyl)ethylamine is described by Blicke, et al., *J. Am. Chem. Soc.*, 64, 3, 477–480 (1942).

Other synthetic approaches to making 2-(2'-thienyl)ethylamine have been disclosed in the art, for example, as described below.

The reduction of 2-(2'-thienyl)acetamide with a hydride, e.g., lithium aluminum hydride to form 2-(2'-thienyl)ethylamine is described in Japanese Kokai J6 1221-184-A.

The electrochemical reduction of 2-(2'-nitrovinyl)thiophene to 2-(2'-amino)-2-ethyl-thiophene is described in UK Patent Application GB 2,013,196A.

The catalytic hydrogenation of thienylacetonitrile to form thienyl ethylamines is described in European Patent No. 274,324.

The reduction of 2-(2-nitrovinyl)thiophene to form 2-(2-thienyl)ethylamine employing a boron-containing reducing agent, preferably diborane is described in U.S. Pat. No. 4,906,756.

The reduction of nitrovinyl thiophenes with a hydride, e.g., lithium aluminum hydride to form thiophene ethylamines is described in *J. Heterocyclic Chem.*, 7, 1257–1268 (1970).

The reduction of arylacetonitriles with lithium aluminum hydride/aluminum chloride to form the corresponding 2-aryl-l-aminoethanes is described in *Synthesis*, 1, 40–42, (1987).

The preparation of thieno[3,2-c]pyridine derivatives, particularly ticlopidine is complicated when the quantities to be prepared are on a large scale. The usefulness of a process for large scale production is gauged by several factors. For example, starting materials have to be available within the purity required; the process must be logistically efficient, e.g., the intermediates should not require isolation or purification (isolation or purification typically result in addition of steps and decrease in yield); and the procedure should return a yield sufficient to make the process commercially feasible. Shortcoming in any of the above parameters result in increased manufacturing costs, which impacts negatively on the desirability of the process. The present invention provides an efficient large scale process for the preparation of thieno[3,2-c]pyridine derivatives, particularly ticlopidine.

SUMMARY OF THE INVENTION

One aspect of the present invention relates to novel compounds having the formula

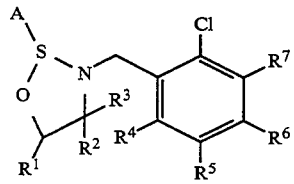

Formula I wherein:

A is oxo or dioxo;

$R^1$, $R^2$ and $R^3$ are independently hydrogen or lower alkyl of one to six carbon atoms; and $R^4$, $R^5$, $R^6$ and $R^7$ are independently hydrogen, lower alkyl of one to six carbon atoms, alkoxy, acyl or halo.

Another aspect of the invention relates to a process for making the compounds of Formula I.

Yet another aspect, the invention relates to a process for the synthesis of substituted benzyl thieno[3,2-c]pyridine derivatives of the following formula:

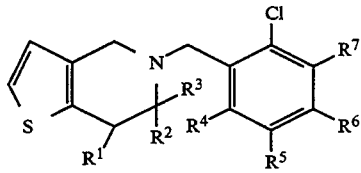

Formula II wherein:

R¹, R² and R³ are independently hydrogen or lower alkyl of one to six carbon atoms;

R⁴, R⁵, R⁶ and R⁷ are independently hydrogen, lower alkyl of one to six carbon atoms, alkoxy, acyl or halo; or a pharmaceutically acceptable salt thereof; from the compounds of Formula I.

In still another aspect, the invention relates to a process for the synthesis of ticlopidine hydrochloride from the compounds of Formula I.

DETAILED DESCRIPTION OF THE INVENTION

Definitions add General Parameters

The following definitions are set forth to illustrate and define the meaning and scope of the various terms used to describe the invention herein.

A "pharmaceutically acceptable acid addition salt" of the thieno[3,2-c]pyridine derivatives may be any salt derived from an inorganic or organic acid, e.g., ticlopidine hydrochloride. The term "pharmaceutically acceptable anion" refers to the anion of such acid addition salts. The salt and/or the anion are chosen not to be biologically or otherwise undesirable. The anions are derived from inorganic acids, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, salicylic acid, methanesulfonic acid, ethanesulfonic acid, p-toluenesulfonic acid and the like.

As used herein, the term "alkyl" refers to monovalent saturated hydrocarbon radicals.

As used herein, the term "lower alkyl" refers to a cyclic, branched or straight chain monovalent alkyl radicals of one to six carbon atoms. This term is further exemplified by such radicals as methyl, ethyl, n-propyl, isopropyl, n-butyl, t-butyl, i-butyl, n-pentyl, cyclopentyl, n-hexyl, or cyclohexyl.

As used herein, the term "alkoxy" refers to the group O—R' where R' is alkyl.

As used herein, the term "lower alkoxy" refers to the group —O—R' where R' is lower alkyl.

As used herein, the term "acyl" refers to the group R'—C(O)— where R' is lower alkyl.

As used herein, the term "halo" refers to fluoro, bromo, chloro and iodo.

As used herein, the term "aryl" refers to a monovalent carbocyclic aromatic moiety, e.g., phenyl and naphthyl.

As used herein, the term "ketone" refers to a compound R—C(O)—R' where R and R' are the same or independently, branched or straight chain lower alkyl, cyclic alkyl or aryl (e.g., acetone, methylethyl ketone, diethyl ketone, cyclohexanone, methylphenylketone and diphenylketone).

As used herein, the terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, ethanol, pyridine, dioxane, xylene, glyme and the like]. Unless specified to the contrary, the solvents used in the reactions of the present invention are inert organic solvents.

As used herein, the term "oxidizing agent" refers to an agent that will remove or accept electrons from a molecule. The agent may be a single compound, such as $RuO_4$, or it may be a combination of compounds such as, a ruthenium salt (e.g., $RuO_2$ or $RuCl_3$) with an oxidizing agent (e.g., sodium hypochlorite, sodium metaperiodate, sodium bromate, chlorine or ceric ammonium nitrate).

As used herein, the term "co-oxidant" refers to an oxidizing agent that reacts with a compound to form another oxidizing agent (e.g., sodium hypochlorite, sodium metaperiodate, sodium bromate, chlorine or ceric ammonium nitrate reacts with $RuO_2$ or $RuCl_3$ to form $RuO_4$).

As used herein, the term "base" refers to compounds that will remove or accept a proton(s) from another molecule, such as, N-methylmorpholine, N-ethylmorpholine, pyridine, dialkylanilines, diisopropylcyclohexylamine, sodium hydroxide, potassium hydroxide, ammonium hydroxide, sodium bicarbonate or potassium bicarbonate.

As used herein, the term "organic base" refers to hydrocarbon bases such as, N-methylmorpholine, N-ethylmorpholine, pyridine, dialkylanilines or diisopropylcyclohexylamine.

As used herein, "leaving group" means an atom or a group, charged or uncharged, that is detachable from another atom in what is considered to be the residual or main part of a molecule, including such leaving groups as, halo, alkyl sulfonates, aryl sulfonates, phosphates, sulfonic acid and sulfonic acid salts.

For the compounds that are the starting material (compounds of Formula 1) for the instant invention the following system will be used for naming said compounds.

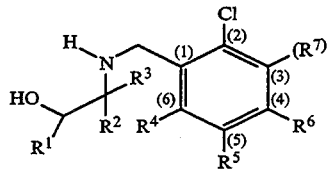

Some representative compounds are named in the following examples.

The compound of Formula 1 where R¹, R², R³, R⁴, R⁵, R⁶ and R⁷ are hydrogen, can be named: N-hydroxyethyl-2-chlorobenzylamine.

The compound of Formula 1 where R¹ is methyl, R⁴ is chloro and R², R³, R⁵, R⁶ and R⁷ are hydrogen, can be named: N-(2-methyl-hydroxyethyl)-2,6-dichlorobenzylamine. Alternatively, the compound can be named following IUPAC convention: N-(2-hydroxy)propyl-2,6-dichlorobenzylamine.

The compound of Formula 1 where R² is methyl, R⁶ is methoxy and R¹, R³, R⁴, R⁵, and R⁷ are hydrogen, can be named: N-(1-methyl-hydroxyethyl)-2-chloro-4- methoxybenzylamine. Alternatively, the compound can be named following IUPAC convention: N-2-(1-hydroxy)propyl-2-chloro-4-methoxybenzylamine.

The compound of Formula 1 where $R^3$ is ethyl, $R^4$ and $R^6$ are chloro and $R^1$, $R^2$, $R^5$, and $R^7$ are hydrogen, can be named: N-(1-ethyl-hydroxyethyl)-2,4,6-trichlorobenzylamine. Alternatively, the compound can be named following IUPAC convention: N-2-(1-hydroxy)butyl-2,4,6-trichlorobenzylamine.

For the compounds of the instant invention containing an oxathiazolidinyl ring moiety (e.g., the compounds of Formula I) the following numbering system will be used for naming said compounds.

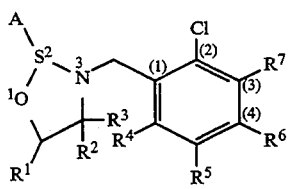

Some representative compounds are named in the following examples.

The compound of Formula I where A is oxo, $R^1$, $R^2$, $R^3$, $R^4$, $R^5$, $R^6$ and $R^7$ are hydrogen, can be named: N-(2-chlorobenzyl)-2-oxo-1,2,3-oxathiazolidine.

The compound of Formula I where A is dioxo, $R^1$, $R^2$, $R^3$, $R^4$, $R^5$, $R^6$ and $R^7$ are hydrogen, can be named: N-(2-chlorobenzyl)-2,2-dioxo-1,2,3-oxathiazolidine.

The compound of Formula I where A is oxo, $R^1$ is methyl, $R^4$ is chloro and $R^2$, $R^3$, $R^5$, $R^6$ and $R^7$ are hydrogen, can be named: N-(2,6-dichlorobenzyl)-2-oxo-5-methyl-1,2,3-oxathiazolidine.

The compound of Formula I where A is dioxo, $R^2$ is methyl, $R^6$ is methoxy and $R^1$, $R^3$, $R^4$, $R^5$, and $R^7$ are hydrogen, can be named: N-(2-chloro-4-methoxy-benzyl)-2,2-dioxo-4-methyl-1,2,3-oxathiazolidine.

The compound of Formula I where A is oxo, $R^3$ is ethyl, $R^4$ and $R^6$ are chloro and $R^1$, $R^2$, $R^5$, and $R^7$ are hydrogen, can be named: N-(2,4,6-trichlorobenzyl)-2-oxo-4-ethyl-1,2,3-oxathiazolidine.

For the compounds of the instant invention containing a thienopyridine moiety (e.g., the compounds of Formula II) the following numbering system will be used for naming said compounds.

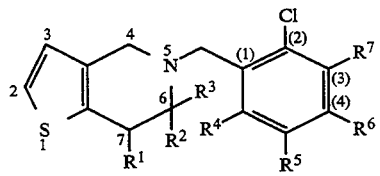

Some representative compounds are named in the following examples.

The compound of Formula II where $R^1$, $R^2$, $R^3$, $R^4$, $R^5$, $R^6$ and $R^7$ are hydrogen, can be named: 5-(2-chlorobenzyl)-4,5,6,7-tetrahydrothieno[3,2-c]pyridine or N-(2-chlorobenzyl)-4,5,6,7-tetrahydrothieno-[3,2-c]pyridine.

The compound of Formula II where $R^1$ is methyl, $R^4$ is chloro and $R^2$, $R^3$, $R^5$, $R^6$ and $R^7$ are hydrogen, can be named: 5-(2,6-dichlorobenzyl)-4,5,6,7-tetrahydro-7-methyl-thieno[3,2-c]pyridine or N-(2,6-dichlorobenzyl)-4,5,6,7-tetrahydro-7-methylthieno[3,2-c]pyridine.

The compound of Formula II where $R^2$ is methyl, $R^6$ is methoxy and $R^1$, $R^3$, $R^4$, $R^5$, and $R^7$ are hydrogen, can be named: 5-(2-chloro-4-methoxybenzyl)-4,5,6,7-tetrahydro-6-methyl-thieno[3,2-c]pyridine or N-(2-chloro-4-methoxybenzyl)-4,5,6,7-tetrahydro-6-methyl-thieno[3,2-c]pyridine.

The compound of Formula II where $R^3$ is ethyl, $R^4$ and $R^6$ are chloro and $R^1$, $R^2$, $R^5$, and $R^7$ are hydrogen, can be named: 5-(2,4,6-trichlorobenzyl)-4,5,6,7-tetrahydro-6-ethyl-thieno[3,2-c]pyridine or N-(2,4,6-trichlorobenzyl)-4,5,6,7-tetrahydro-6-ethylthieno[3,2-c]pyridine.

Unless specified to the contrary, the reactions described herein take place at atmospheric pressure over a temperature range from about 10° C. to about 100° C., more preferably from about 10° C. to about 50° C., and most preferably at about room (or "ambient") temperature, e.g., about 20° C.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

As used herein, the term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

As used herein, the term "effective amount" means a dosage sufficient to provide treatment for the disease state being treated. This will vary depending on the patient, the disease and the treatment being effected. See, for example, U.S. Pat. No. 4,051,141 to Castaigne (the pertinent portions of which are incorporated herein by reference), for a detailed description of the anti-inflammatory activity, vaso-dilator activity, and inhibitory activity on blood plate aggregation of the thieno[3,2-c]pyridine derivatives made according to the present invention, as well as the description of toxicological and pharmacological investigations therefor.

Synthesis of the Compounds of Formulae I and II

The compounds of Formulae I and II are synthesized as described with reference to Reaction Scheme A. As used in Reaction Scheme A, the substituents A, $R^1$, $R^2$, $R^3$, $R^4$, $R^5$, $R^6$ and $R^7$ are the same as described in the Summary of The Invention.

The first step of Reaction Scheme A illustrates a cyclization reaction of the compounds of Formula 1 to form the compounds of Formula I where A is oxo.

The second step of Reaction Scheme A illustrates a oxidation of the compounds of Formula I where A is oxo to form the compounds of Formula I where A is dioxo.

The third step of Reaction Scheme A illustrates a condensation of 2-thienyllithium with the compounds of Formula I where A is dioxo to form the compounds of Formula 2.

The fourth step of Reaction Scheme A illustrates a cyclization reaction of the compounds of Formula 2 to form the compounds of Formula II.

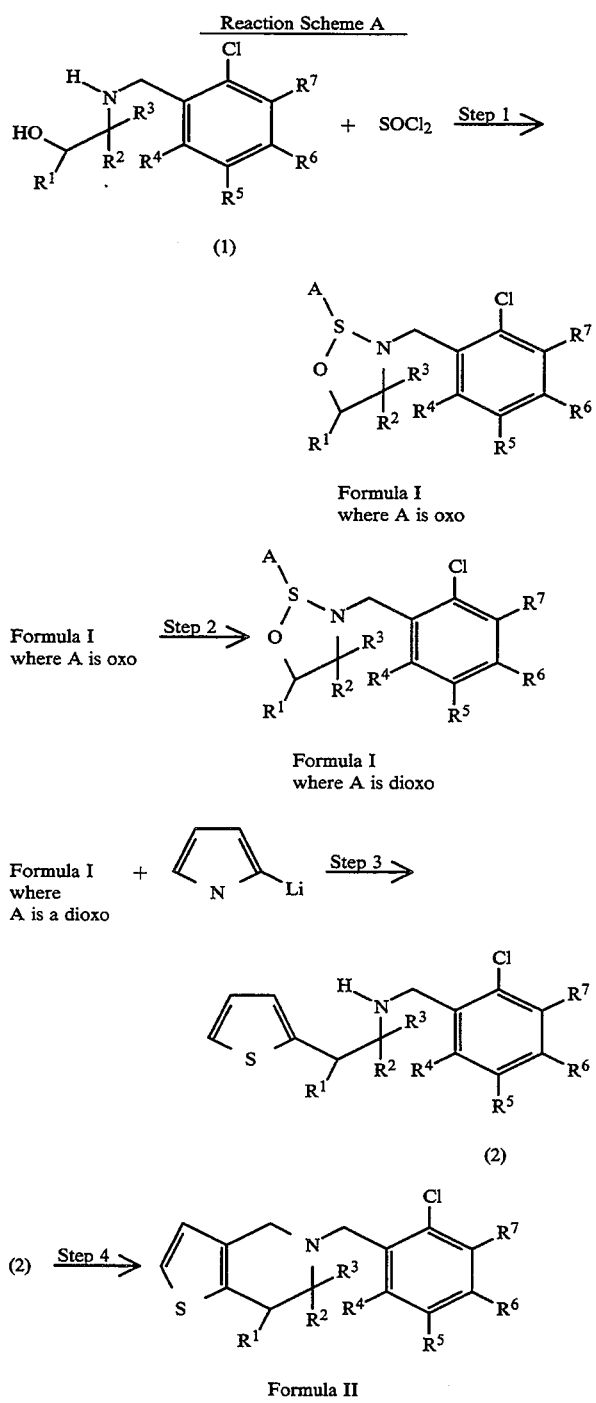

Preparation of the Compounds of Formula I, Where A is oxo

Referring to Reaction Scheme A, the starting materials (the compounds of Formula 1) are substituted N-hydroxyethyl-2-chlorobenzylamine compounds, such as N-hydroxyethyl-2-chlorobenzylamine, N-hydroxyethyl-2-chloro-6-methylbenzylamine, N-(2-methylhydroxyethyl)-2-chlorobenzylamine, N-(1-ethylhydroxyethyl)-2,6-dichlorobenzylamine, N-(2,2-dimethyl-hydroxyethyl)-2-chloro-4-methoxybenzylamine, and N-(1-ethyl-2-methylhydroxyethyl)-2-chloro-6-methylbenzylamine. Many of these materials are available commercially from such suppliers as, Aldrich Chemical Company or Sigma Chemical Company. Alternatively, they can be easily prepared according to procedures that are well known to the art and published in the literature, such as, U.S. Pat. No. 2,732,402, the pertinent portions of which are incorporated herein by reference.

As illustrated in Reaction Scheme A, a substituted N-hydroxyethyl-2-chlorobenzylamine compound (a compound of Formula 1) is dissolved in a solvent (such as ethyl acetate, isopropyl acetate, methylene chloride, 1,2-dichloroethane, chloroform or pyridine, preferably ethyl acetate). About 2 molar equivalents of an organic base (such as pyridine, N-methylmorpholine, N-ethylmorpholine, diisopropylcyclohexylamine or triethylamine, preferably N-methylmorpholine) dissolved in a solvent (e.g., ethyl acetate, isopropyl acetate, methylene chloride, 1,2-dichloroethane, chloroform or pyridine, preferably ethyl acetate) and thionyl chloride (about 1 molar equivalent) dissolved in a solvent (e.g., ethyl acetate, isopropyl acetate, methylene chloride, 1,2-dichloroethane, chloroform or pyridine, preferably ethyl acetate) is added to the solution with stirring. The solution is refluxed at the reflux temperature of the solvent used for about 30 minutes. The liquid phase is separated and washed in succession in an acid solution (e.g., hydrochloric acid, sulfuric acid or acetic acid, preferably in hydrochloric acid), water and an aqueous base solution (e.g., sodium carbonate, dilute sodium hydroxide or sodium bicarbonate, preferably sodium carbonate). The resulting substituted 2-oxo-1,2,3-oxathiazolidinyl compound (Formula I where A is oxo) can be isolated by removal of the solvents. Preferably, the compound so-obtained is directly converted (without further isolation or purification) to the corresponding compound of Formula I where A is dioxo by following the procedure described in the second step of Reaction Scheme A.

Preparation of the Compounds of Formula I Where A is Dioxo

A substituted 2-oxo-1,2,3-oxathiazolidinyl compound (a compound of Formula I where A is oxo) is dissolved in a solvent (e.g., ethyl acetate, isopropyl acetate, methylene chloride or 1,2-dichloroethane, preferably ethyl acetate). About 0.0010 molar equivalents of a ruthenium salt (such as, $RuO_2$ or $RuCl_3$, preferably $RuO_2$), an aqueous solution of a base (e.g., sodium bicarbonate or potassium bicarbonate, preferably sodium bicarbonate) and about 1.3 molar equivalents of a co-oxidant (such as, sodium hypochlorite, sodium metaperiodate, sodium bromate, chlorine or ceric ammonium nitrate, preferably sodium hypochlorite) combined to form an oxidizing agent are added to the 2-oxo-1,2,3-oxathiazolidinyl solution. The solution is stirred for about 5 to 45 minutes, preferably about 15 minutes and is allowed to warm on its own. An alcohol (e.g., isopropanol, isobutanol or ethanol, preferably isopropanol) is added to the solution to quench the excess oxidant and to return the $RuO_2$ for recycling. The solution is stirred for about 15 to 60 minutes, preferably about 35 minutes. The solution is filtered and washed with a suitable solvent (e.g., ethyl acetate, isopropyl acetate, methylene chloride, 1,2-dichloroethane, chloroform or pyridine, preferably ethyl acetate). The desired substituted 2,2-dioxo-1,2,3- oxathiazolidinyl compounds (Formula I where A is dioxo) are purified by removal of the solvents or, they can be used without further purification for the preparation of the compounds of Formula 2.

Alternative Preparation of Compounds of Formula I Where A is Dioxo

A substituted N-hydroxyethyl-2-chlorobenzylamine (a compound of Formula 1) is dissolved in a dry solvent (e.g., methylene chloride, 1,2-dichloroethane, carbon tetrachloride, benzene, toluene or pyridine, preferably methylene chloride). About 2 molar equivalents of an organic base (such as, pyridine, N-methylmorpholine, N-ethylmorpholine, dialkylanilines, or diisopropylcyclohexylamine, preferably pyridine) is added to the solution. The solution is cooled and maintained at a temperature in the range of $-30°$ to $-60°$ C., preferably about $-45°$ C. to $-50°$ C. About 1 molar equivalent of sulfuryl chloride dissolved in a solvent (e.g., 1,2-dichloroethane, carbon tetrachloride, benzene or toluene, preferably methylene chloride) is added to the solution in a gradual manner, preferably dropwise over a period of about 20 minutes. After the addition, the solution is stirred for a period of about 1 to 2 hours, preferably about 90 minutes at a temperature in the range of about $-30°$ C. to $60°$ C., preferably about $-45°$ C. to $-50°$ C. The solution is then allowed to warm to a temperature in the range of about $0°$ C. to $20°$ C., preferably about $5°$ to $10°$ C. over a period of about 1 to 2 hours, preferably about 90 minutes. The desired substituted 2,2-dioxo-1,2,3-oxathiazolidinyl compounds (Formula I where A is dioxo) are purified and isolated by removal of the solvents followed by silica gel chromatography or the like.

Preparation of the Compounds of Formula 2

A substituted 2,2-dioxo-1,2,3-oxathiazolidinyl compound (Formula I where A is dioxo) is dissolved in a dried solvent (e.g., diethyl ether or tetrahydrofuran, preferably tetrahydrofuran) under an inert atmosphere (e.g., nitrogen or argon, preferably nitrogen). The solution is cooled to a temperature in the range of about $0°$ C. to $-100°$ C., preferably about $-78°$ C. As the solution is stirred, about 1.15 molar equivalents of thienyllithium dissolved in a solvent (such as, diethyl ether, tetrahydrofuran, preferably tetrahydrofuran) is added in a gradual manner, preferably dropwise. The solution is stirred for about 15 minutes and a dilute acid solution (e.g., 5% hydrochloric acid, 5% hydrobromic acid, preferably 5% hydrochloric acid) is added. The solution is allowed to warm to room temperature and is stirred for about 12 to 36 hours, preferably about 24 hours. The resulting substituted N-(2-chlorobenzyl)-2-(2-thienyl)ethylamine compounds (compounds of Formula 2) are isolated as their hydrochloride salts by removal of the solvents or they can be used in the preparation of thieno[3,2-c]pyridine derivatives (the compounds of Formula II), particularly ticlopidine.

Preparation of the Compounds of Formula II

The compounds of Formula II are prepared by dissolving a correspondingly substituted N-(2-chlorobenzyl)-2-(2-thienyl)ethylamine compound (a compound of Formula 2) in a solvent (e.g., dimethylformamide or dimethylsulfoxide, preferably dimethylformamide) and contacting it with about 2-4 molar equivalents of formaldehyde or a formaldehyde equivalent (such as, dimethoxymethane or trioxane, preferably dimethoxy]nethane) and about 1.2 molar equivalents of an acid [e.g., hydrogen chloride (gas) or sulfuric acid, preferably hydrogen chloride (gas)]. The solution is refluxed and stirred for a period of about 6 to 24 hours, preferably about 12 hours. The solvent is removed under vacuum while maintaining the temperature of the solution at less than $85°$ C. A base (e.g., sodium hydroxide, potassium hydroxide or ammonium hydroxide, preferably sodium hydroxide) dissolved in water and a solvent (e.g., toluene, benzene or xylene, preferably toluene) is added to the residue and stirred at a temperature in the range of about $45°$ to $65°$ C., preferably below $55°$ C. for a period of about 15 to 60 minutes, preferably about 30 minutes. The aqueous and organic layers are separated and the aqueous layer washed with an organic solvent (e.g., toluene, benzene or xylene, preferably toluene). The organic layer is combined with the solvent from the aqueous layer washing and concentrated under vacuum to a volume of about 50ml. Residual salts are removed by centrifugation or filtration, preferably filtration. A solvent (e.g., methanol, ethanol or isopropanol, preferably methanol) and an acid [such as, hydrogen chloride (gas), where the acid used will determine the acid addition salt of the Formula II, e.g., hydrogen chloride (gas) will result in the hydrochloride salt of Formula II] is added to the purified solution at a temperature below $50°$ C. until the solution has a pH of about 1 to 2, preferably about 1.5. The solution is heated to a temperature of about $40°$ to $60°$ C., preferably about $50°$ C. for a period of about 30 to 90 minutes, preferably about one hour and then cooled to a temperature of about $-10°$ to $10°$ C., preferably about $0°$ C. for a period of about 30 to 90 minutes, preferably about one hour. The desired corresponding substituted thieno[3,2.c]pyridinyl acid addition salts are purified and isolated by removal of the solvents followed by extraction or the like.

Alternate Preparations of Formula II Cyclization with dimethoxymethane

Alternatively, compounds of Formula II may be cyclized from the corresponding substituted compounds of Formula 2 with dimethoxymethane under the conditions described in U.S. Pat. No. 4,174,448, the pertinent portions of which are incorporated herein by reference.

Cyclization with paraformaldehyde, trioxane or formaldehyde

Alternatively, the compounds of Formula 2 may be cyclized to form the compounds of Formula II using reagents such as paraformaldehyde, trioxane or formaldehyde under the conditions described in U.S. Pat. No. 4,127,580, the pertinent portions of which are incorporated herein by reference.

Preparation of the Free Base Compounds of Formula II

The acid addition salts of the compounds of Formula II may be converted to the corresponding free bases by treating with an excess of a suitable base, such as ammonia or sodium bicarbonate, typically in the presence of aqueous solvent, and at a temperature of about $0°$ C. to $50°$ C. The free base form is isolated by conventional means, such as extraction with an organic solvent.

Preferred Compounds

Presently preferred is the compound of Formula I where A is oxo; and $R^1$, $R^2$, $R^3$, $R^4$, $R^5$, $R^6$ and $R^7$ are hydrogen, i.e., N-(2-chlorobenzyl)-2-oxo-1,2,3-oxathiazolidine.

Also preferred is the compound of Formula I where A is dioxo; and $R^1$, $R^2$, $R^3$, $R^4$, $R^5$, $R^6$ and $R^7$ are hydrogen, i.e., N-(2-chlorobenzyl)-2,2-dioxo-1,2,3-oxathiazolidine.

The preferred compound made by the process of the invention is 5-(2-chlorobenzyl)-4,5,6,7-tetrahydrothieno[3,2-c]pyridine hydrochloride, which is also known as ticlopidine hydrochloride.

Preferred Processes and Last Steps

A preferred process for making N-(2-chlorobenzyl)-2-oxo-1,2,3-oxathiazolidine entails contacting N-hydroxyethyl-2-chlorobenzylamine with thionyl chloride.

A preferred process for making N-(2-chlorobenzyl)-2,2-dioxo-1,2,3-oxathiazolidine entails contacting N-(2-chlorobenzyl)-2-oxo-1,2,3-oxathiazolidine with an oxidizing agent.

A preferred process for making the acid addition salt of ticlopidine comprises the steps of:

a. contacting N-hydroxyethyl-2-chlorobenzylamine with sulfuryl chloride and an organic base to give N-(2-chlorobenzyl)-2,2-dioxo-1,2,3-oxathiazolidine, and b. converting the N-(2-chlorobenzyl)-2,2-dioxo-1,2,3-oxathiazolidine to the acid addition salt of ticlopidine.

A most preferred process for making the acid addition salt of ticlopidine comprises the steps of:

a. contacting N-hydroxyethyl-2-chlorobenzylamine with thionyl chloride and an organic base to give N-(2-chlorobenzyl)-2-oxo-1,2,3-oxathiazolidine, and b. converting the N-(2-chlorobenzyl)-2-oxo-1,2,3-oxathiazolidine to the acid addition salt of ticlopidine.

In the above-described most preferred process for making the acid addition salt of ticlopidine, further preferred is the process wherein the step of converting the N-(2-chlorobenzyl)-2-oxo-1,2,3-oxathiazolidine to the acid addition salt of ticlopidine comprises the steps of:

c. contacting the N-(2-chlorobenzyl)-2-oxo-1,2,3-oxathiazolidine with ruthenium dioxide hydrate and aqueous sodium hypochlorite to give N-(2-chlorobenzyl)-2,2-dioxo-1,2,3-oxathiazolidine, d. contacting the N-(2-chlorobenzyl)-2,2-dioxo-1,2,3-oxathiazolidine with thienyllithium to give N-(2-chlorobenzyl)-2-(2-thienyl)ethylamine, and e. contacting the N-(2-chlorobenzyl)-2-(2-thienyl)ethylamine with dimethoxymethane and an acid to give the acid addition salt of ticlopidine.

In the above-described most preferred process for making the acid addition salts of ticlopidine, especially preferred is the process wherein the acid addition salt is the hydrochloride salt, i.e., ticlopidine hydrochloride.

EXAMPLES

The following preparations and examples are given to enable those skilled in the art to more clearly understand and to practice the present invention. They should not be considered as limiting the scope of the invention, but merely as being illustrative and representative thereof.

EXAMPLE 1

Preparation of N-(2-chlorobenzyl)-2-oxo-1,2,3-oxathiazolidine

Formula I Where A is Oxo; and $R^1$, $R^2$, $R^3$, $R^4$, $R^5$, $R^6$ and $R^7$ are Hydrogen N-hydroxyethyl-2-chlorobenzylamine (5.0g, 26.93mmole) in ethyl acetate (50ml) was stirred at room temperature (24° C.) in a reaction vessel fitted with a calcium chloride ($CaCl_2$) drying tube. N-methylmorpholine (5.58g, 55.21mmole) was added to the solution while it was stirring. Thionyl chloride (3.27g, 27.47mmole) in ethyl acetate (17.5ml) was then likewise added over 15 minutes and washed with ethyl acetate (2ml). The solution was refluxed for 30 minutes. $H_2O$ (10ml) was added and the mixture was stirred for 5 minutes. The organic phase was separated and washed successively with 1N HCl (10ml), $H_2O$ (10ml) and saturated aqueous $NaHCO_3$ (10ml). N-(2-chlorobenzyl)-2-oxo-1,2,3-oxathiazolidine was recovered as an oil by drying and evaporation of the solvent. Characteristic analytical data are it: 1156cm$^{-1}$; $^1$H NMR $CDCl_3$: $\delta$7.46-7.28 (aromatic 4H), 4.80'4.77 (—O—$CH_2$1H) , 4.43–4.40 (benzylic 1H) , 4.37–4.32 (—O—$CH_2$1H) , 4.16–4.13 (benzylic 1H) , 3.52–3.48 (—N—$CH_2$1H) and 3.34–3.29 (—N—$CH_2$1H); and $^{13}$C NMR $CDCl_3$: $\delta$134.23, 133.85, 130.41, 129.87, 129.35, 127.07 (aromatic) , 71.50 (—O—$CH_2$) , 47.40 (benzylic) and 47.19 (—N—$CH_2$) .

1B. Preparation of Other Compounds of Formula I, Where A is Oxo

By following the procedures of Example 1A and substituting N-hydroxyethyl-2-chlorobenzylamine with the following:

N-hydroxyethyl-2-chloro-6-methylbenzylamine,
N-(2-methyl-hydroxyethyl)-2-chlorobenzylamine,
N-(1-ethyl-hydroxyethyl)-2,6-dichlorobenzylamine,
N-(2,2-dimethyl-hydroxyethyl)-2-chloro-4-methoxybenzylamine, and
N-(1-ethyl-2-methyl-hydroxyethyl)-2-chloro-6-methylbenzylamine; there are obtained the following respective compounds:

N-(2-chloro-6-methylbenzyl)-2-oxo-1,2,3-oxathiazolidine,
N-(2-chlorobenzyl)-2-oxo-5-methyl-1,2,3-oxathiazolidine,
N-(2,6-dichlorobenzyl)-2-oxo-4-ethyl-1,2,3-oxathiazolidine,
N-(2-chloro-4-methoxybenzyl)-2-oxo-4,4-dimethyl-1,2,3-oxathiazolidine, and
N-(2-dichloro-6-methylbenzyl)-2-oxo-4-methyl-5-ethyl-1,2,3-oxathiazolidine.

EXAMPLE 2

Preparation of N-(2-chlorobenzyl)-2,2-dioxo-1,2,3-oxathiazolidine

2A. Formula I Where A is dioxo; and $R^1$, $R^2$, $R^3$, $R^4$, $R^5$, $R^6$ and $R^7$ are Hydrogen To a solution of N-(2-chlorobenzyl)-2-oxo-1,2,3-oxathiazolidine (6.25g, 26.93mmole) prepared, for example, as described in Example 1A, in ethyl acetate (70ml) was added saturated aqueous sodium bicarbonate (31.8ml) and ruthenium dioxide hydrate (4.1mg, 0.0217mmole) while the solution was stirred vigorously. Commercial bleach (52.8ml, 5.25% sodium hypochlorite) was then added. The solution was stirred for 15 minutes and warmed on its own to 34° C. Isopropanol (2.75ml) was added with vigorous stirring, after which the solution was stirred for 35 minutes. The solution was filtered through Celite and the filter cake was washed with ethyl acetate. The aqueous phase was removed and the organic phase washed with 10% aqueous $Na_2S_2O_3$. The organic phase was filtered through a bed of $MgSO_4$ and washed in with ethyl acetate. The solvent was removed by evaporation under vacuum at 40° C. yielding a clear oil. The oil was triturated twice with hexanes, and the product, N-(2-chlorobenzyl)-2,2-dioxo-1,2,3-oxathiazolidine, was recovered as an off-white waxy solid (5.54g, 22.36mmole). Recrystallization of a sample from methyl t-butyl ether gave a white crystalline solid. Characteristic analytical data are mp: 62.5°–64.5° C.; ir: 1336, 1184, 917, 802 cm$^{-1}$; $^1$H NMR CHCl$_3$: δ7.54–7.25 (aromatic 4H) , 4.55 (t, J=6.5) (—O—CH$_2$2H), 4.39 (—N—CH$_2$ benzylic 2H) , 3.53 (t, J=6.5) (—N—CH$_2$2H); and $^{13}$C NMR CDCl$_3$: δ134.19, 132.22, 130.71, 129.90, 129.86, 127.34 (aromatic), 66.69 (—O—CH$_2$) , 48.85 (benzylic) and 47.76 (—N—CH$_2$).

2B. Alternative Preparation of Formula I Where A is dioxo, and R$^1$, R$^2$, R$^3$, R$^4$, R$^5$, R$^6$ and R$^7$ are Hydrogen To a solution of N-hydroxyethyl-2-chlorobenzylamine (1.86g, 10.0mmole) in dry methylene chloride (6ml) in a reaction vessel fitted with a calcium chloride (CaCl$_2$) drying tube was added dry pyridine (1.66ml, 20.5mmole). The solution was stirred and cooled to −50° C. Sulfuryl chloride (1.35g, 10.0mmole) dissolved in dry methylene chloride (4ml) was added dropwise over 20 minutes while the temperature of the solution was maintained between −45° C. and −50° C. The solution was stirred at −50° C. for 90 minutes and then allowed to warm to 8° C over 90 minutes. The entire reaction mixture was poured onto a silica gel bed (30g), slurry-packed in a 60ml Type "C" sintered glass funnel. The bed was eluted with methylene chloride while collecting 40ml fractions. Fractions containing the product were combined and the solvent removed by evaporation under vacuum at 40° C. yielding N-(2-chlorobenzyl)-2,2-dioxo-1,2,3-oxathiazolidine as a clear oil (0.40g, 1.85mmole), which crystallized. Characteristic analytical data are mp. 61°–62.5° C.; and NMR spectra similar to those of Example 2A (above).

2C. Preparation of Other Compounds of Formula I, Where A is Dioxo

By following the procedures of Example 2A or 2B and substituting N-(2-chlorobenzyl)-2-oxo-1,2,3-oxathiazolidine with the following:

N-(2-chloro-6-methylbenzyl)-2-oxo-1,2,3-oxathiazolidine,
N-(2-chlorobenzyl)-2-oxo-5-methyl-1,2,3-oxathiazolidine,
N-(2,6-dichlorobenzyl)-2-oxo-4-ethyl-1,2,3-oxathiazolidine,
N-(2-chloro-4-methoxybenzyl)-2-oxo-4,4-dimethyl1,2,3-oxathiazolidine, and
N-(2-dichloro-6-methylbenzyl)-2-oxo-4-methyl-5-ethyl1,2,3-oxathiazolidine; there are obtained the following respective compounds:

N-(2-chloro-6-methylbenzyl)-2,2-dioxo-1,2,3-oxathiazolidine,
N-(2-chlorobenzyl)-2,2-dioxo-5-methyl-1,2,3-oxathiazolidine,
N-(2,6-dichlorobenzyl)-2,2-dioxo-4-ethyl-1,2,3-oxathiazolidine,
N-(2-chloro-4-methoxybenzyl)-2,2-dioxo-4,4-dimethyl1,2,3-oxathiazolidine, and
N-(2-dichloro-6-methylbenzyl)-2,2-dioxo-4-methyl-5-ethyl-1,2,3-oxathiazolidine.

EXAMPLE 3

Preparation of N-(2-chlorobenzyl)-2-(2-thienyl)-ethylamine hydrochloride

3A. Formula 2 Where R$^1$, R$^2$, R$^3$, R$^4$, R$^5$, R$^6$ and R$^7$ are Hydrogen N-(2-chlorobenzyl)-2,2-dioxo-1,2,3-oxathiazolidine (5.54g, 22.36mmole) was dissolved in dry THF (27ml) with stirring at room temperature (24° C.) under nitrogen. The solution was cooled in a dry ice/acetone bath. Thienyllithium in THF (1.09M, 23.6ml, 25.72mmole) was added dropwise to the solution under nitrogen and washed with THF (2ml). After 15 minutes the ice bath was removed, 5% hydrochloric acid (40ml) was added and the solution was stirred at room temperature (24° C.) overnight. THF was removed by evaporation under vacuum at 40° C. The residue was cooled in an ice bath for 30 minutes and filtered. A solid material was recovered and washed with ice water (5×10ml) and dried under vacuum to yield a gray-green crumbly solid (4.37g, 15.16mmole). Partial evaporation of the filtrate gave an additional 0.41g (1.42mmole) product after similar filtration, washing and drying.

The total solid material was dissolved in acetone (12ml) and refluxed for 5 minutes. The slurry was cooled to room temperature and then cooled in an ice bath for 20 minutes. The slurry was filtered, washed with ice cold acetone (3×6ml), and dried under vacuum to give N-(2-chlorobenzyl)-2-(2-thienyl)-ethylamine hydrochloride (3.74g, 12.98mmole) as a chalky greenish-gray solid.

3B. Preparation of Other Compounds of Formula 2

By following the procedures of Example 3A and substituting N-(2-chlorobenzyl)-2,2-dioxo-1,2,3-oxathiazolidine with the following:

N-(2-chloro-6-methylbenzyl)-2,2-dioxo-1,2,3-oxathiazolidine,
N-(2-chlorobenzyl)-2,2-dioxo-5-methyl-1,2,3-oxathiazolidine,
N-(2,6-dichlorobenzyl)-2,2-dioxo-4-ethyl-1,2,3-oxathiazolidine,
N-(2-chloro-4-methoxybenzyl)-2,2-dioxo-4,4-dimethyl-1,2,3-oxathiazolidine, and
N-(2-dichloro-6-methylbenzyl)-2,2-dioxo-4-methyl-5-ethyl-1,2,3-oxathiazolidine; there are obtained the following respective compounds:

N-(2-chloro-6-methylbenzyl)-2-(2-thienyl)-ethylamine,
N-(2-chlorobenzyl )-2-(2-thienyl )-2-methyl-ethylamine,
N-(2,6-dichlorobenzyl )-2-(2-thienyl )-1-ethylethylamine,
N-(2-chloro-4-methoxybenzyl )-2- (2-thienyl )-1,1-dimethyl-ethylamine, and
N-(2-dichloro-6-methylbenzyl)-2-(2-thienyl )-1-methyl-2-ethyl-ethylamine.

EXAMPLE 4

Preparation of Ticlopidine Hydrochloride

4A. Formula II Where R$^1$, R$^2$, R$^3$, R$^4$, R$^5$, R$^6$ and R$^7$ are Hydrogen N-(2-chlorobenzyl )-2-(2-thienyl)-ethylamine hydrochloride (29.2g, 102mmole), hydrogen chloride gas (4.5g, 129mmoles) and dimethoxymethane (33ml, 388mmoles) were combined in dimethylformamide (57ml). The solution was refluxed and stirred for 11 hours. The dimethylformamide was removed under vacuum while keeping the temperature of the solution at 85° C. A solution of sodium hydroxide (11g, 275mmoles) in H$_2$O (87ml) and toluene (87ml) was added to the residue and stirred at a temperature less than 55° C. for 30 minutes. The aqueous and organic layers were separated and the aqueous layer washed with toluene (85ml). The toluene was combined with the organic layer and concentrated under vacuum to 50ml. The solution was filtered to remove salts. Methanol (17ml) and HCl gas were added to the solution at a temperature less than 40° C. until a pH of 1.5 was reached. The slurry was heated to a temperature less than 50° C. for one hour and cooled to 0° C. for one hour. The product was isolated, washed with 1:9 methanol/toluene and dried; yielding 87.6% real to real (corrected for assay of starting material) of 5-(2-chlorobenzyl)-4,5,6,7-tetrahydrothieno[3,2-c]pyridine hydrochloride (ticlopidine hydrochloride). Characterizing HPLC data indicated 99.3% pure.

4B. Preparation of Other Compounds of Formula II

By following the procedures of Example 4A and substituting for N-(2-chlorobenzyl)-2-(2-thienyl)-ethylamine hydrochloride with the following:

N-(2-chloro-6-methylbenzyl)-2-(2-thienyl)-ethylamine,

N-(2-chlorobenzyl)-2-(2-thienyl)-2-methyl-ethylamine,

N-(2,6-dichlorobenzyl)-2-(2-thienyl)-l-ethylethylamine,

N-(2-chloro-4-methoxybenzyl)-2-(2-thienyl)-1,1-dimethyl-ethylamine, and

N-(2-dichloro-6-methylbenzyl)-2-(2-thienyl)-1-methyl-2-ethyl-ethylamine; there are obtained the following respective compounds:

5-(2-chloro-6-methylbenzyl)-4,5,6,7-tetrahydro-thieno[3,2-c]pyridine hydrochloride, 5 -(2-chlorobenzyl)-4,5,6,7-tetra-7-methylhydro-thieno[3,2-c]pyridine hydrochloride, 5 -(2,6-dichlorobenzyl)-4,5,6,7-tetra-6-ethylhydro-thieno[3,2-c]pyridine hydrochloride, 5 -(2-chloro-4-methoxybenzyl)-4,5,6,7-tetra-6,6dimethyl-hydrothieno[3,2-c]pyridine hydrochloride, and 5 -(2-dichloro-6-methylbenzyl)-4,5,6,7-tetra-6-methyl--7-ethyl -hydrothieno[3,2-c]pyridine hydrochloride.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula:

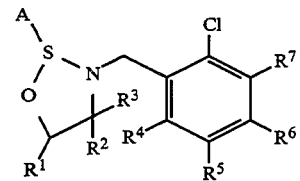

wherein:

A is oxo or dioxo;

R$^1$, R$^2$ and R$^3$ are independently hydrogen or lower alkyl of one to six carbon atoms;

R$^4$, R$^5$, R$^6$ and R$^7$ are independently hydrogen, lower alkyl of one to six carbon atoms, alkoxy, acyl or halo.

2. The compound of claim 1 wherein R$^1$, R$^2$, R$^3$, R$^4$, R$^5$, R$^6$ and R$^7$ are hydrogen.

3. The compound of claim 1 wherein A is oxo.

4. The compound of claim 3 wherein R$^1$, R$^2$, R$^3$, R$^4$, R$^5$, R$^6$ and R$^7$ are hydrogen.

5. The compound of claim 1 wherein A is dioxo.

6. The compound of claim 5 wherein R$^1$, R$^2$, R$^3$ R$^4$, R$^5$, R$^6$ and R$^7$ are hydrogen.

* * * * *